(12) United States Patent
Anno

(10) Patent No.: US 7,356,119 B2
(45) Date of Patent: Apr. 8, 2008

(54) X-RAY EXAMINATION METHOD AND APPARATUS

(75) Inventor: Hidero Anno, Otawara (JP)

(73) Assignees: Kabushiki Kaisha Toshiba, Tokyo (JP); Toshiba Electron Tubes & Devices Co., Ltd., Tokyo (JP)

( * ) Notice: Subject to any disclaimer, the term of this patent is extended or adjusted under 35 U.S.C. 154(b) by 10 days.

(21) Appl. No.: 11/522,475

(22) Filed: Sep. 18, 2006

(65) Prior Publication Data
US 2007/0009094 A1 Jan. 11, 2007

Related U.S. Application Data

(63) Continuation of application No. PCT/JP2005/012602, filed on Jul. 7, 2005.

(30) Foreign Application Priority Data
Jul. 7, 2004 (JP) .............................. 2004-200359

(51) Int. Cl.
*G01N 23/04* (2006.01)
(52) U.S. Cl. .............................. 378/62; 378/37; 378/70
(58) Field of Classification Search .................. 378/11, 378/14–17, 37, 51–62, 70, 119, 125, 143, 378/144–146; 382/132
See application file for complete search history.

(56) References Cited

U.S. PATENT DOCUMENTS 5,787,146 A * 7/1998 Giebeler ...................... 378/82
6,934,409 B2 * 8/2005 Ohara ......................... 382/132
7,027,556 B2 * 4/2006 Ohara ......................... 378/62
7,062,015 B2 * 6/2006 Lewis ......................... 378/84
7,190,761 B1 * 3/2007 Honda et al. ................. 378/62

FOREIGN PATENT DOCUMENTS

JP          01-161645          6/1989

(Continued)

OTHER PUBLICATIONS

International Search Report dated Oct. 4, 2005 for Appln. No. PCT/JP2005/012602 filed Jul. 7, 2005.

(Continued)

*Primary Examiner*—Jurie Yun
(74) *Attorney, Agent, or Firm*—Pillsbury Winthrop Shaw Pittman, LLP

(57) ABSTRACT

An X-ray examination method comprises setting a tube voltage of an X-ray tube to a tube voltage that makes an X-ray absorptance difference between a first X-ray propagation medium and a second X-ray propagation medium in an object become not more than 10%, applying an X-ray beam from the X-ray tube to the object while a tube voltage of the X-ray tube is set to the tube voltage, and detecting a transmitted X-ray image including an X-ray refraction image formed in a region along a contour of a boundary surface between the first X-ray propagation medium and the second X-ray propagation medium by refraction of the X-ray beam by the boundary surface in superimposition on an X-ray absorption image reflecting the X-ray absorbing power difference between the first X-ray propagation medium and the second X-ray propagation medium.

19 Claims, 18 Drawing Sheets

FOREIGN PATENT DOCUMENTS

| | | |
|---|---|---|
| JP | 07-143400 | 6/1995 |
| JP | 2000-245731 | 9/2000 |
| JP | 2001-194738 | 7/2001 |
| JP | 2003-010162 | 1/2003 |
| JP | 2004-147917 | 5/2004 |

OTHER PUBLICATIONS

Gureyev T.E. et al., "Hard x-ray quantitative non-interferometric phase-contrast microscopy"; J. Phys. D, 1999, vol. 32, No. 5, pp. 563-567.

* cited by examiner

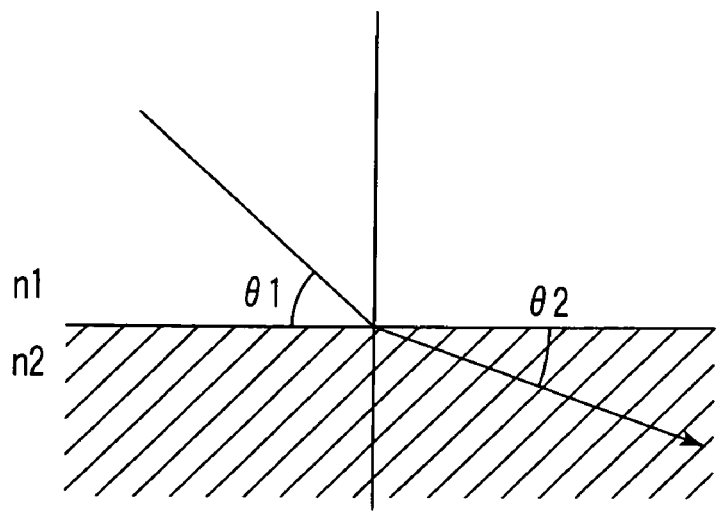
$\cos\theta 1/\cos\theta 2 = n2/n1$
$= (1-\delta 2)/(1-\delta 1) \sim 1-(\delta 2-\delta 1)$
F I G. 4
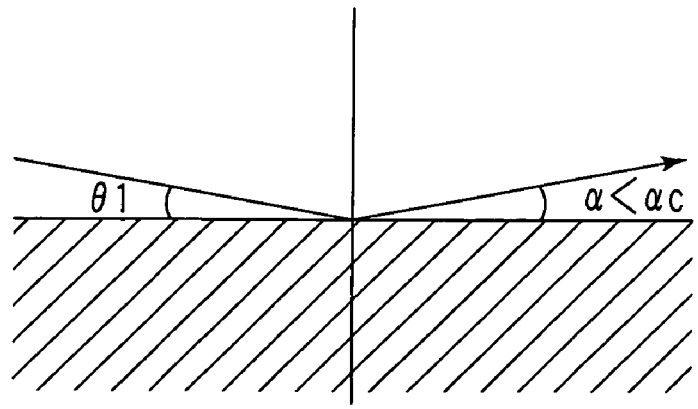
$\alpha c = \sqrt{2(\delta 2-\delta 1)}$
$= \sqrt{(5.4/10 \cdot \lambda^2)} \sqrt{(Z2\rho 2/A2)-(Z1\rho 1/A1)}$
F I G. 5

| X-ray energy (kev) | Acrylic resin ||| Silica glass ||| $\Delta\mu = \mu p - \mu a$ (cm$^{-1}$) |
|---|---|---|---|---|---|---|---|
| | Mass attenuation coefficient (cm²/g) | Density (g/cm³) | Linear absorption coefficient $\mu a$ (cm$^{-1}$) | Mass attenuation coefficient (cm²/g) | Density (g/cm³) | Linear absorption coefficient $\mu a$ (cm$^{-1}$) | |
| 10 | 3.31 | | 3.94 | 17.1 | | 38.13 | 34.19 |
| 15 | 1.07 | | 1.27 | 5.11 | | 11.4 | 10.13 |
| 20 | 0.555 | | 0.66 | 2.24 | | 5 | 4.34 |
| 30 | 0.3 | | 0.36 | 0.785 | | 1.75 | 1.39 |
| 40 | 0.233 | 1.19 | 0.28 | 0.43 | 2.23 | 0.96 | 0.68 |
| 50 | 0.205 | | 0.24 | 0.299 | | 0.67 | 0.43 |
| 60 | 0.191 | | 0.23 | 0.241 | | 0.54 | 0.31 |
| 80 | 0.176 | | 0.209 | 0.19 | | 0.424 | 0.215 |
| 100 | 0.165 | | 0.196 | 0.166 | | 0.37 | 0.174 |

FIG. 7

| X-ray energy (kev) | Δt · Δμ | | | | | |
|---|---|---|---|---|---|---|
| | In case of Δt = 0.01 (cm) | In case of Δt = 0.02 (cm) | In case of Δt = 0.04 (cm) | In case of Δt = 0.06 (cm) | In case of Δt = 0.08 (cm) | In case of Δt = 0.10 (cm) |
| 15 | 0.101 | 0.203 | 0.405 | 0.608 | 0.81 | 1.013 |
| 20 | 0.043 | 0.087 | 0.174 | 0.26 | 0.347 | 0.434 |
| 30 | 0.014 | 0.028 | 0.056 | 0.083 | 0.111 | 0.139 |
| 40 | 0.007 | 0.014 | 0.027 | 0.041 | 0.054 | 0.068 |
| 50 | 0.004 | 0.009 | 0.017 | 0.026 | 0.034 | 0.043 |
| 60 | 0.003 | 0.006 | 0.012 | 0.019 | 0.025 | 0.031 |
| 80 | 0.002 | 0.004 | 0.008 | 0.013 | 0.017 | 0.021 |
| 100 | 0.002 | 0.003 | 0.007 | 0.001 | 0.014 | 0.017 |

FIG. 9

| X-ray energy (kev) | $\mu$ (cm) | t=3 (cm) | | t=4 (cm) | | t=5 (cm) | |
|---|---|---|---|---|---|---|---|
| | | $\exp(-\mu \cdot t)$ | Incident dose (relative value) that makes transmitted dose equal to transmitted dose with 20 kev | $\exp(-\mu \cdot t)$ | Incident dose (relative value) that makes transmitted dose equal to transmitted dose with 20 kev | $\exp(-\mu \cdot t)$ | Incident dose (relative value) that makes transmitted dose equal to transmitted dose with 20 kev |
| 15 | 1.27 | 0.022 | 6.3 | 0.006 | 11.8 | 0.002 | 18.5 |
| 20 | 0.66 | 0.138 | 1 | 0.071 | 1 | 0.037 | 1 |
| 30 | 0.36 | 0.34 | 0.41 | 0.237 | 0.3 | 0.165 | 0.22 |
| 40 | 0.28 | 0.432 | 0.32 | 0.326 | 0.22 | 0.247 | 0.15 |
| 50 | 0.24 | 0.487 | 0.28 | 0.383 | 0.19 | 0.301 | 0.12 |
| 60 | 0.23 | 0.502 | 0.27 | 0.399 | 0.18 | 0.317 | 0.12 |
| 80 | 0.209 | 0.534 | 0.26 | 0.433 | 0.16 | 0.352 | 0.11 |
| 100 | 0.196 | 0.555 | 0.25 | 0.457 | 0.16 | 0.375 | 0.1 |

FIG. 13

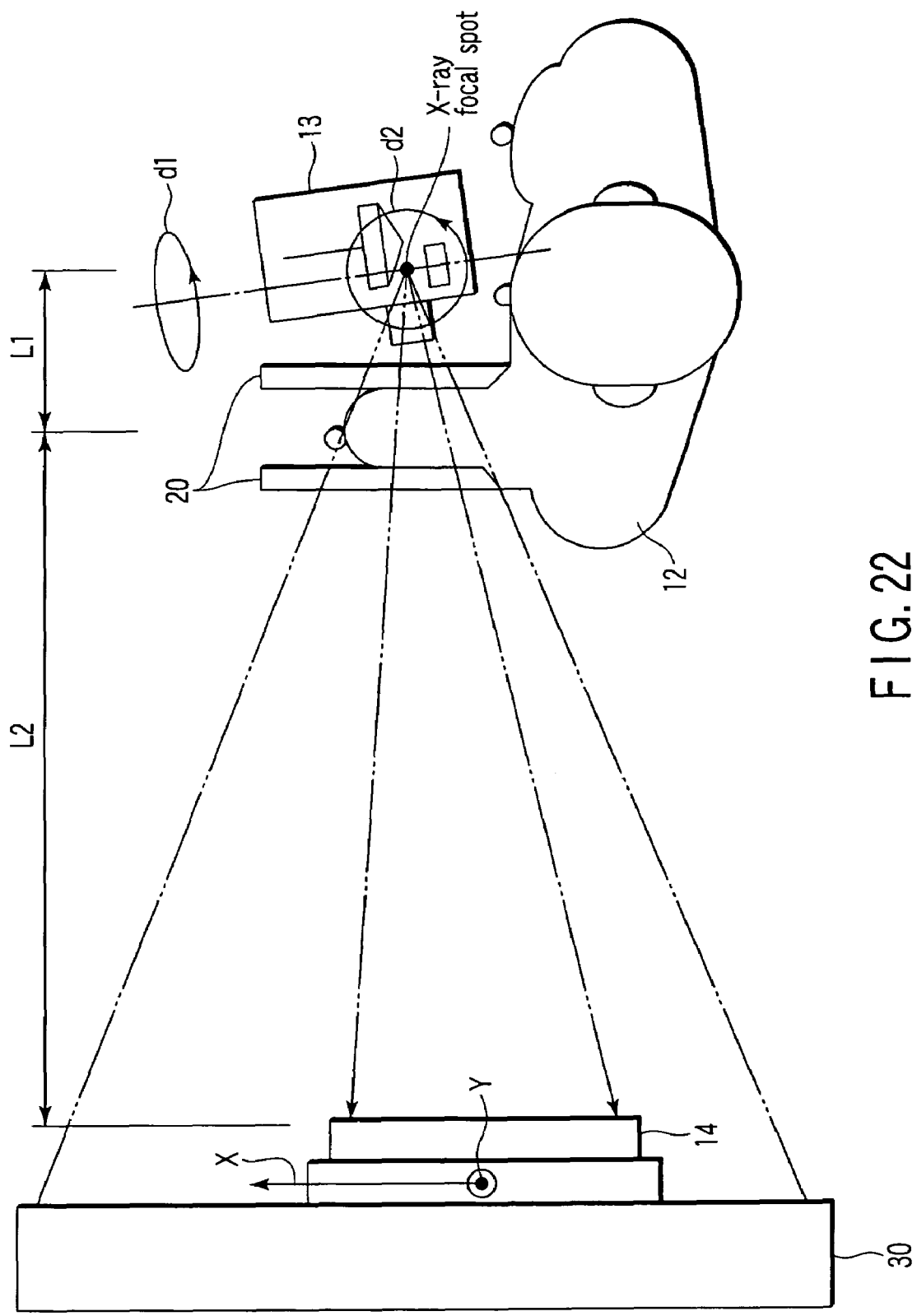
F I G. 22

X-RAY EXAMINATION METHOD AND APPARATUS

CROSS-REFERENCE TO RELATED APPLICATIONS

This is a Continuation Application of PCT Application No. PCT/JP2005/012602, filed Jul. 7, 2005, which was published under PCT Article 21(2) in Japanese.

This application is based upon and claims the benefit of priority from prior Japanese Patent Application No. 2004-200359, filed Jul. 7, 2004, the entire contents of which are incorporated herein by reference.

BACKGROUND OF THE INVENTION

1. Field of the Invention

The present invention relates to an X-ray examination method and apparatus which are used in the fields of medical diagnosis and non-destructive examination.

2. Description of the Related Art

Conventionally, an X-ray examination apparatus such as an X-ray diagnostic apparatus or X-ray CT apparatus applies an X-ray beam emitted from an X-ray tube to an object and detects a transmitted X-ray image transmitted through the object by using a detector or the like, thereby visualizing an X-ray absorption image as a transmitted X-ray image which reflects the X-ray absorbing power difference between different X-ray propagation media contained in the object, as disclosed in, for example, Jpn. Pat. Appln. KOKAI Publication No. 1-161645 (pp. 2-3).

Recently, attention has been paid to a new imaging principle of obtaining an image component of an X-ray refraction image which contour-enhances a boundary portion between different X-ray propagation media in superimposition on a general X-ray absorption image based on an X-ray absorbing power difference by using a technique of reducing the focal spot formed by an X-ray tube in combination with a technique of performing enlargement radiography by increasing the distance between an object and a detector as disclosed in, for example, Jpn. Pat. Appln. KOKAI Publication No. 2001-194738 (pp. 2-3, FIGS. 1 and 2). According to this imaging principle, an X-ray refraction image is formed in a region along the contour of the boundary surface between different X-ray propagation media in an object by the refraction of an X-ray beam by the boundary surface owing to the refractive index difference between the different X-ray propagation media. This imaging principle exhibits an improving effect of obtaining a clearer image and allowing identification of finer substances than in the prior art.

In the field of soft tissue medical diagnosis using mammography and the like, a screen-film system, storage fluorescent substance, or solid-state imaging device is generally used as a detector, and a low-energy X-ray beam is used by setting the tube voltage of an X-ray tube to as low as 20 to 39 kVp. In particular, a low-energy X-ray beam containing a characteristic X-ray of molybdenum (MO) or rhodium (RH) as a main component is generally used by using an X-ray tube using molybdenum (MO) or rhodium (RH) as an anode target. Using a low-energy X-ray beam makes it possible to obtain an identifiable absorption contrast even with respect to an abnormality which exhibits a relatively small X-ray absorbing power difference from neighboring normal tissue, e.g., an anomalous tissue in the breast.

In the field of non-destructive examination, when X-ray examination is to be performed on a foreign substance or a void (a cavity filled with air) inside a thick object, since it is necessary to ensure a transmitted X-ray dose with a sufficient intensity, the tube voltage of an X-ray tube is increased to increase the effective energy of incident X-rays as compared with a case of a thin object.

DISCLOSURE OF INVENTION

As described above, in the field of soft tissue medical diagnosis using mammography and the like, setting the tube voltage of an X-ray tube to as low as 20 to 39 kVp and using a low-energy X-ray beam make it possible to obtain an identifiable image contrast even with respect to an abnormality which exhibits a relatively small X-ray absorbing power difference from neighboring normal tissue, e.g., an anomalous tissue in the breast. However, as the tube voltage of the X-ray tube is increased to 39 kVp or more to increase the energy of X-rays, the X-ray absorbing power of a human body decreases, and an absorption contrast due to an X-ray absorbing power difference cannot be obtained, resulting in difficulty in identifying the image. Such an image which is difficult to identify has been regarded as useless.

It is generally known that in X-ray diagnosis, as the energy of X-rays decreases, the exposure dose of a patient increases. This is based on the physical phenomenon that as the energy of X-rays decreases, the X-ray absorbing power of the human body increases, and the transmitted X-ray dose decreases. That is, although an image is formed by detecting transmitted X-rays, since an image with less noise can be obtained as the transmitted X-ray dose increases, a predetermined transmitted X-ray dosage is required to obtain image quality with a similar noise level. For this reason, the incident X-ray dose is increased as the energy of X-rays decreases.

For such reasons, in the field of soft tissue medical diagnosis using mammography and the like, since imaging is performed at the low tube voltage of an X-ray tube in principle, it is difficult to decrease the exposure dose by increasing the tube voltage.

In addition, in the field of soft tissue medical diagnosis using mammography and the like, if an object is thicker than usual, imaging needs to be performed at a higher tube voltage than that in a case of a thin object. As a result, the identifying power with respect to minute abnormalities such as calcified substances decreases.

In the field of medical diagnosis, when X-ray examination is to be performed on a blood vessel, renal pelvis system, gallbladder, bile duct, oviduct, lymphatic system, alimentary canal, bronchus, or the like, it is necessary to increase the X-ray absorbing power difference from neighboring tissue by injecting a contrast medium such as an iodine compound. However, the injection of a contrast medium becomes a burden.

In the field of non-destructive examination, when X-ray examination is to be performed on a foreign substance or a void (a cavity filled with air) inside a thick object, since it is necessary to ensure a transmitted X-ray dose with a sufficient intensity, the tube voltage of an X-ray tube is increased to increase the effective energy of incident X-rays as compared with a case of a thin object. Assume that the effective energy of incident X-rays is increased. In this case, if a foreign substance, a void, or the like is small in size, or the X-ray absorbing power difference between the foreign substance, the void, or the like and a surrounding normal region is small, the transmitted X-ray intensity difference is small, and the identifying power may decrease. The identifying power decreases with an increase in thickness. Therefore, exceeding a given thickness threshold leads to difficulty in identifying the image.

The present invention has been made in consideration of this point, and has as its object to provide an X-ray examination method and apparatus which can realize a reduction in exposure dose and reliably detect even a small abnormality or the like in the field of medical diagnosis, and can reliably detect the internal structure of even a thick object in the field of non-destructive examination.

BRIEF SUMMARY OF THE INVENTION

According to an aspect of the present invention, there is provided an X-ray examination method comprises: setting a tube voltage of an X-ray tube to a tube voltage that makes an X-ray absorptance difference between a first X-ray propagation medium and a second X-ray propagation medium with an X-ray absorbing power different from that of the first X-ray propagation medium in an object become not more than 10%; applying an X-ray beam from the X-ray tube to the object while a tube voltage of the X-ray tube is set to the tube voltage; and detecting a transmitted X-ray image including an X-ray refraction image formed in a region along a contour of a boundary surface between the first X-ray propagation medium and the second X-ray propagation medium by refraction of the X-ray beam by the boundary surface in superimposition on an X-ray absorption image reflecting the X-ray absorbing power difference between the first X-ray propagation medium and the second X-ray propagation medium.

According to another aspect of the present invention, there is provided an X-ray examination apparatus comprises: an X-ray tube which applies an X-ray beam to an object and in which a tube voltage is set to make an X-ray absorptance difference between a first X-ray propagation medium and a second X-ray propagation medium with an X-ray absorbing power different from that of the first X-ray propagation medium in an object become not more than 10%; a detector which detects a transmitted X-ray image transmitted through the object; and an arrangement adjusting unit which sets a distance between the X-ray tube and the object and a distance between the object and the detector so as to obtain the transmitted X-ray image including an X-ray refraction image formed in a region along a contour of a boundary surface between the first X-ray propagation medium and the second X-ray propagation medium by refraction of the X-ray beam by the boundary surface in superimposition on an X-ray absorption image reflecting the X-ray absorbing power difference between the first X-ray propagation medium and the second X-ray propagation medium.

According to still another aspect of the present invention, there is provided an X-ray examination apparatus comprises: an X-ray tube which applies an X-ray beam to an object; and a detector which detects a transmitted X-ray image transmitted through the object, wherein an application direction of the X-ray beam is adapted to be changed by rotating the X-ray tube about a focal position such that the object is adapted to be divisionally imaged a plurality of times while an application range of the X-ray beam is changed.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a view for explaining the refraction of an X-ray by the boundary surface between different X-ray propagation media;

FIG. 5 is a view for explaining the total reflection of an X-ray by the boundary surface between different X-ray propagation media;

FIG. 7 is a table showing the characteristics of acrylic resin and a silica glass ball with respect to different tube voltages of the X-ray tube of the above X-ray examination apparatus, i.e., different X-ray energies;

FIG. 9 is a table showing X-ray absorptance differences, i.e., absorption contrasts, with respect to different tube voltages of the X-ray tube, i.e., different X-ray energies, and the size of a silica glass ball;

FIG. 13 is a table showing X-ray transmittances and incident doses in the relationship between different tube voltages of the X-ray tube, i.e., different X-ray energies, and the size of a silica glass ball;

FIG. 22 is a plan view showing a modification of the mammography apparatus shown in FIG. 17.

DETAILED DESCRIPTION OF THE INVENTION

An X-ray examination method and apparatus according to the first embodiment of the present invention will be described in detail below with reference to the views of the accompanying drawing.

Figure 1:
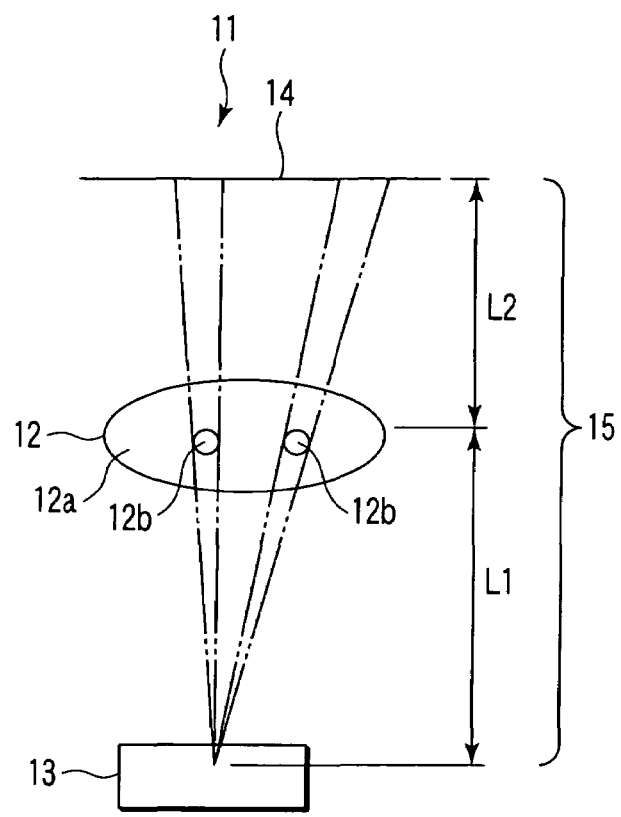
FIG. 1 is a view for explaining an example of imaging performed by an X-ray examination apparatus according to the first embodiment of the present invention.

FIG. 1 shows an example of imaging by an X-ray examination apparatus 11. The X-ray examination apparatus 11 comprises an X-ray tube 13 which applies an X-ray beam to an object 12, a detector 14 which detects a transmitted X-ray image transmitted through the object 12, and an arrangement adjusting unit 15 which sets a distance L1 between the X-ray tube 13 and the object 12 and a distance L2 between the object 12 and the detector 14 to allow enlargement radiography.

The X-ray tube 13 comprises, for example, a rotor structure having a rotation axis provided with a focus formation plane inside a vacuum vessel, a stationary structure which is coaxially fitted to the rotor structure and rotatably holds the rotor structure, a bearing mechanism provided on the fitting portion between the rotor structure and the stationary structure, and a coil which generates a rotating magnetic field for applying a rotating force to the rotor structure. For example, as the X-ray tube 13, a rotating anode X-ray tube is used, which is formed such that finishing on the focus formation plane of a rotor structure and finishing on a surface of the rotor structure which is coaxially fitted to a stationary structure are performed as coaxial processing.

This rotating anode X-ray tube is provided with a control unit which stops the generation of a rotating magnetic field from the coil for at least part of the period during which X-rays are emitted to perform imaging. In addition, the dimensions of the effective focal spot formed by the rotating anode X-ray tube in the vertical and horizontal directions are 100 µm or less, and the diametrical clearance of the bearing for rotating the rotating anode is 50 µm or less. A slide bearing using a liquid metal as a lubricant is used as the bearing of the rotating anode X-ray tube, and a path for a coolant which directly cools the stationary structure is provided inside the stationary structure.

The anode target of the X-ray tube 13 is made of tungsten or a material containing 50 at % of tungsten.

In addition, as the detector 14, for example, one of the following are used: an X-ray storage fluorescent screen, an X-ray image tube, an imaging unit which senses an output fluorescent image from the X-ray image tube, and a solid-state imaging device which senses an X-ray image.

When an X-ray image tube is used, for example, its input fluorescent film is a fluorescent film containing cesium iodide as a base material, and the thickness of an X-ray beam in the transmission direction falls within the range of 100 to 500 µm.

As a solid-state imaging device, one of the following is used: a direct solid-state imaging device which directly converts X-rays into an electrical signal and an indirect solid-state imaging device which converts X-rays into light through a fluorescent film and then converts the light into an electrical signal. The fluorescent film of the indirect solid-state imaging device is a fluorescent film containing, for example, cesium iodide as a base material, and the thickness of an X-ray beam from the film in the transmission direction preferably falls within the range of 100 to 500 µm.

The arrangement adjusting unit 15 adjusts the distances L1 and L2 so as to obtain a transmitted X-ray image having an X-ray refraction image formed in a region along the contour of the boundary surface between different X-ray propagation media contained in the object 12 by the refraction of an X-ray beam by the boundary surface in superimposition on an X-ray absorption image which reflects the X-ray absorbing power difference between the different X-ray propagation media.

Figure 2:
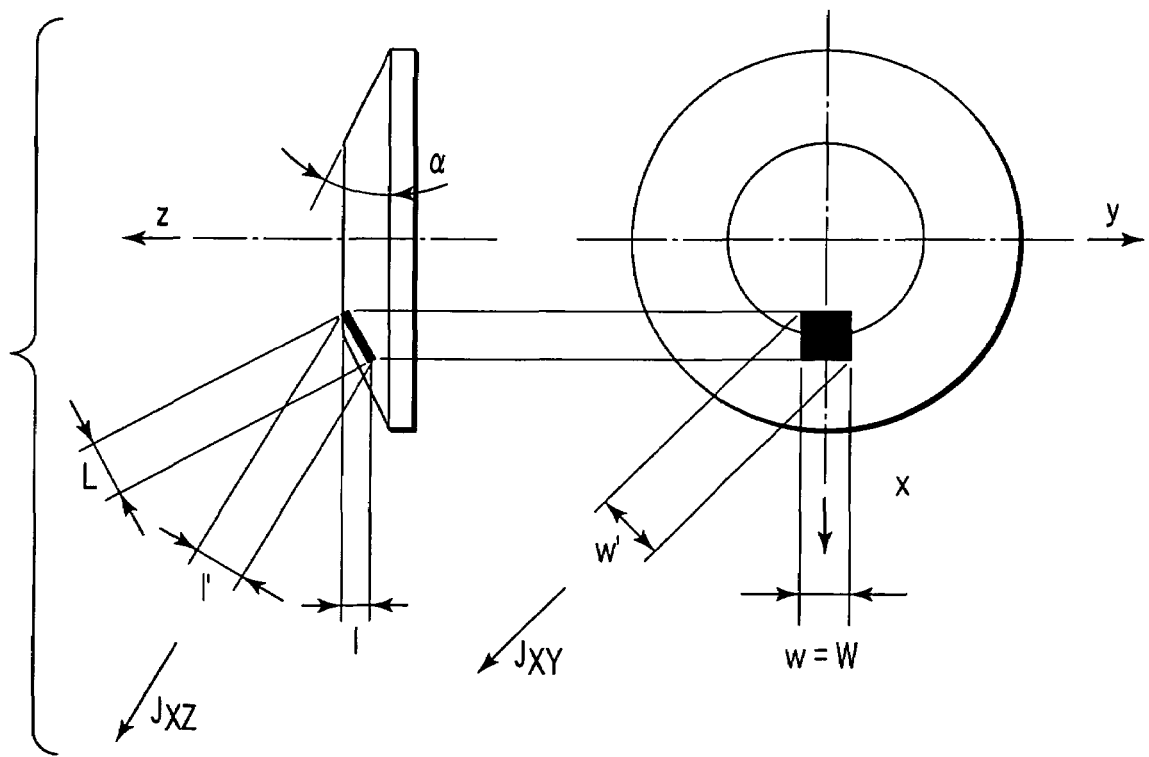
FIG. 2 is a view for explaining the effective size of an X-ray focal spot viewed from an arbitrary direction in an X-Z plane view and X-Y plane view of an object shown in FIG. 1.

In this case, as shown in FIG. 2, letting p(J) be the maximum span dimension of a projection image (an effective focal spot viewed from a given application direction J) of an X-ray focal spot which is transmitted through the object 12 in the application direction J, and P is a set of p(J) throughout all application directions of the X-ray transmitted through the object 12, p(J)<100 µm preferably hold for all the directions J and maximum (P)/minimum (P)<2.

The symbols shown in FIG. 2 represent the following:

L: focal length
l: effective focal length
l': effective focal length viewed from direction J
W: focal width
w: effective focal width
w': effective focal width viewed from direction J
$J_{XZ}$: projection vector onto X-Y plane in J
$J_{XY}$: projection vector onto X-Y plane in J
α: target angle For example, the object 12 comprises a base material portion and a foreign material portion such as a material which is covered by the base material portion and has a smaller refractive index with respect to X-rays than the base material portion, or comprises a base material portion and a foreign material portion such as a material, gas, or vacuum which is covered by the base material member and has a larger refractive index with respect to X-rays than the base material portion.

Figure 3:
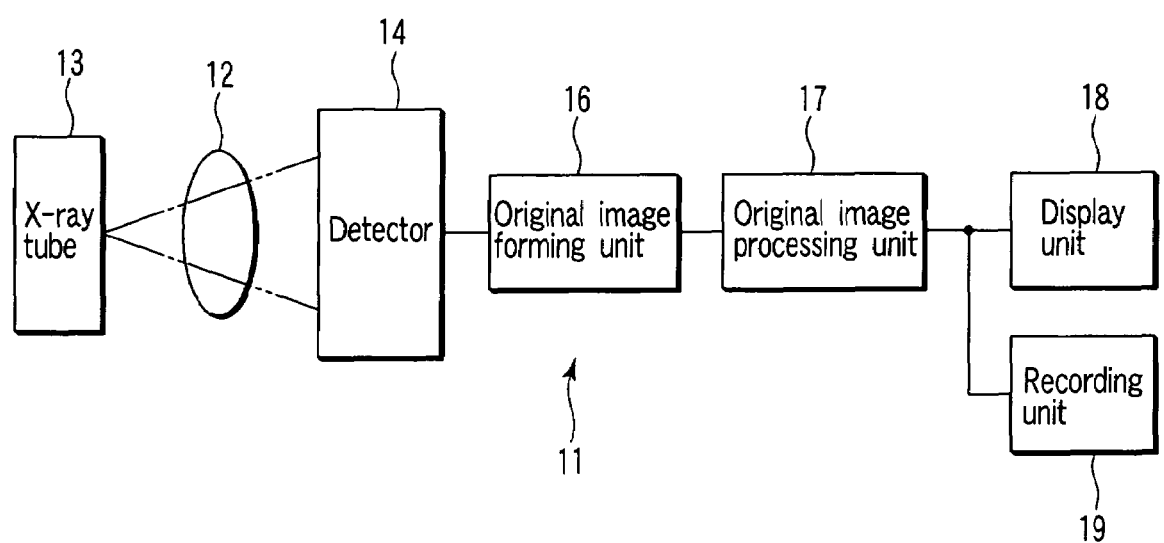
FIG. 3 is a view showing the arrangement of the above X-ray examination apparatus.

FIG. 3 is a view showing the arrangement of the X-ray examination apparatus 11. The X-ray examination apparatus 11 comprises an original image forming unit 16 which forms an original image from the transmitted X-ray image detected by the detector 14, an image processing unit 17 which extracts an X-ray refraction image component in the original image of the transmitted X-ray image formed by the original image forming unit 16, a display unit 18 which displays the X-ray refraction image component extracted by the image processing unit 17, and a recording unit 19 which records the X-ray refraction image component.

The image processing unit 17 includes, for example, frequency enhancement processing of enhancing the high-frequency component of an original image of a transmitted X-ray image and subtraction processing of at least partially subtracting a background image from which an X-ray refraction image is excluded from an original image.

At least part of the background image used in the above subtraction processing is an image obtained by enhancing the low-frequency component of an original image by frequency enhancement processing, an image obtained by sampling pixels more roughly than for an original image, or an image obtained by smoothing a digital image obtained by sampling pixels more roughly than for an original image by using an approximate curved surface (e.g., a two-dimensional polynomial approximated by using the least squares method).

FIGS. 4 and 5 quantitatively show changes in angle as X-rays are refracted and totally reflected by the boundary surface between different X-ray propagation media.

A refractive index n of X-rays in an X-ray propagation medium is represented as follows by approximation in disregard of X-ray absorption by the X-ray propagation medium.

n=1−δ

δ=2.7·10$^{10}$·Z·ρ·λ$^2$/A

Z: atomic number
A: atomic weight
λ: wavelength (cm) of X-rays
ρ: density (g/cm$^3$)

In general, δ is a small value of about $10^{-7}$ to $10^{-6}$.

The number of electrons in 1 g Z element (atomic weight A) is represented by NZ/A where N is Avogadro's number. Z/A of hydrogen is 1, and that of other elements is about 0.5. Consideration should be given to this when the values Z/A of a compound or mixture are averaged. For example, with respect to acrylic resin ($C_5H_8O$), Z/A=(8/14)+0.5×(6/14) =11/14. With respect to silica glass ($SiO_2$), Z/A =0.5.

The refractive indexes of X-ray propagation media 1 and 2 are represented by n1 and n2, values δ are represented by δ1 and δ2, and δ=δ2−δ1. The relative refractive index set when X-rays strike from the X-ray propagation medium 1 to the X-ray propagation medium 2 is represented by n2/n1=(1−δ2)/(1−δ1)∼1−(δ2−δ1)=1−Δδ.

If δ2>δ1, X-rays can be totally reflected by the boundary surface, a maximum value (critical angle) αc of total reflection α is represented by αc={2(δ2−δ1)}$^{1/2}$=(5.4/10$^{10}$·λ2)$^{1/2}${(Z2ρ2/A2)−(Z1ρ1/A1)}$^{1/2}$.

X-ray examination on a model obtained by embedding a silica glass ball 12b as the second X-ray propagation medium with a diameter of 0.1 to 1.0 mm in acrylic resin 12a as the first X-ray propagation medium serving as the object 12 will be described next. In this case, the acrylic resin 12a differs in X-ray absorbing power from the silica glass ball 12b. This model corresponds to a breast containing a minute calcified substance.

Figure 6:
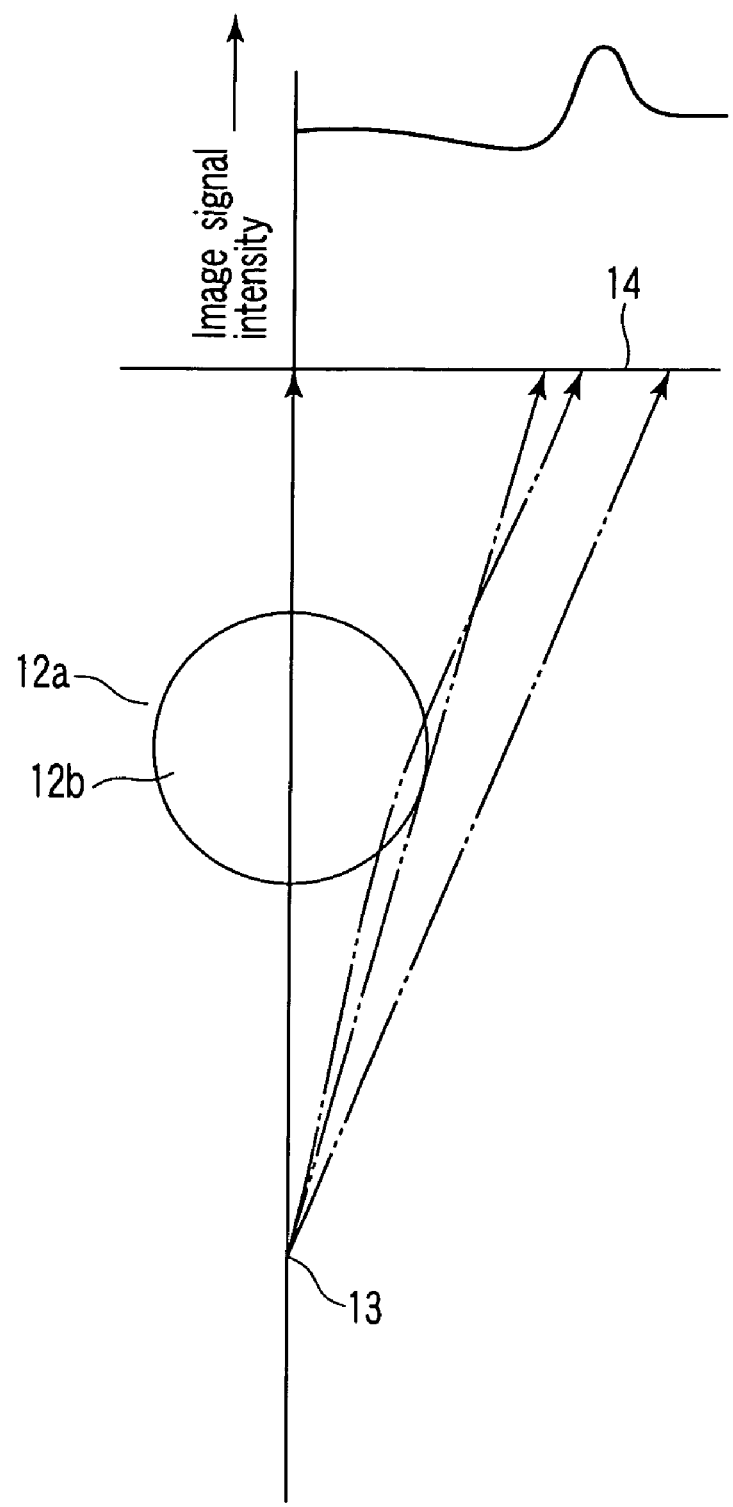
FIG. 6 is a view for explaining a transmitted X-ray image detected by the detector of the above X-ray examination apparatus.

As shown in FIG. 6, when an X-ray beam is applied from the X-ray tube 13 to the object 12, the detector 14 detects a transmitted X-ray image obtained by superimposition of an X-ray absorption image reflecting the X-ray absorbing power difference between the acrylic resin 12a and the silica glass ball 12b in the object 12 and an X-ray refraction image formed in a region along the contour of the boundary surface between the acrylic resin 12a and the silica glass ball 12b by refraction of the X-ray beam by the boundary surface.

The path of the X-ray beam which has struck near the boundary surface between the acrylic resin 12a and the silica glass ball 12b deviates to the acrylic resin 12a portion located outside due to a refraction effect. For this reason, in the transmitted X-ray image of the silica glass ball 12b which is detected by the detector 14, a contour with a high X-ray intensity is formed on the acrylic resin 12a side, and a contour with a low X-ray intensity is formed on the silica glass ball 12b side. The maximum intensity of this contour or the difference between the maximum intensity and the minimum intensity appears as an X-ray refraction image component. This phenomenon is schematically shown in FIG. 6. The phenomenon can be presented by performing ray tracing simulation at the interface exhibiting a refractive index difference.

Let E be the distance between a contour portion exhibiting the maximum X-ray intensity and a contour portion exhibiting the minimum X-ray intensity.

According to Jpn. Pat. Appln. KOKAI Publication No. 2001-194738, the distance E is represented by equation (1) given below:

$$E=2.3(1+L2/L1)^{1/3}·(L2·Δδ·d^{1/2})^{2/3} \quad (1)$$

where d is the diameter (m) of the silica glass ball 12b, and Δδ is the refractive index difference between the acrylic resin 12a and the silica glass ball 12b. The measurement unit for the value of L2 is also "m".

According to the above patent reference, letting S be the focal spot size of the X-ray tube 13 (a length parallel to a line segment of the distance E), and ε be the resolution of the detector 14 (the minimum identification size), when inequalities (2) and (3) given below hold, an X-ray refraction image component can be identified.

$$9E \geq S(L2/L1) \quad (2)$$

$$9E \geq \epsilon \quad (3)$$

With respect to a combination of arbitrary values of S, ε, L1, and L2, it can be estimated by using expressions (1) to (3) whether an X-ray refraction image component can be identified.

FIG. 7 shows the characteristics of the acrylic resin 12a and silica glass ball 12b with respect to different X-ray energies. Both the acrylic resin 12a and silica glass ball 12b exhibit a larger linear absorption coefficient with respect to a lower X-ray energy, and vice versa. With regard to a linear absorptance difference Δμ between the acrylic resin 12a and silica glass ball 12b as well, as the X-ray energy decreases, the linear absorptance difference Δμ increases, and vice versa.

Figure 8:
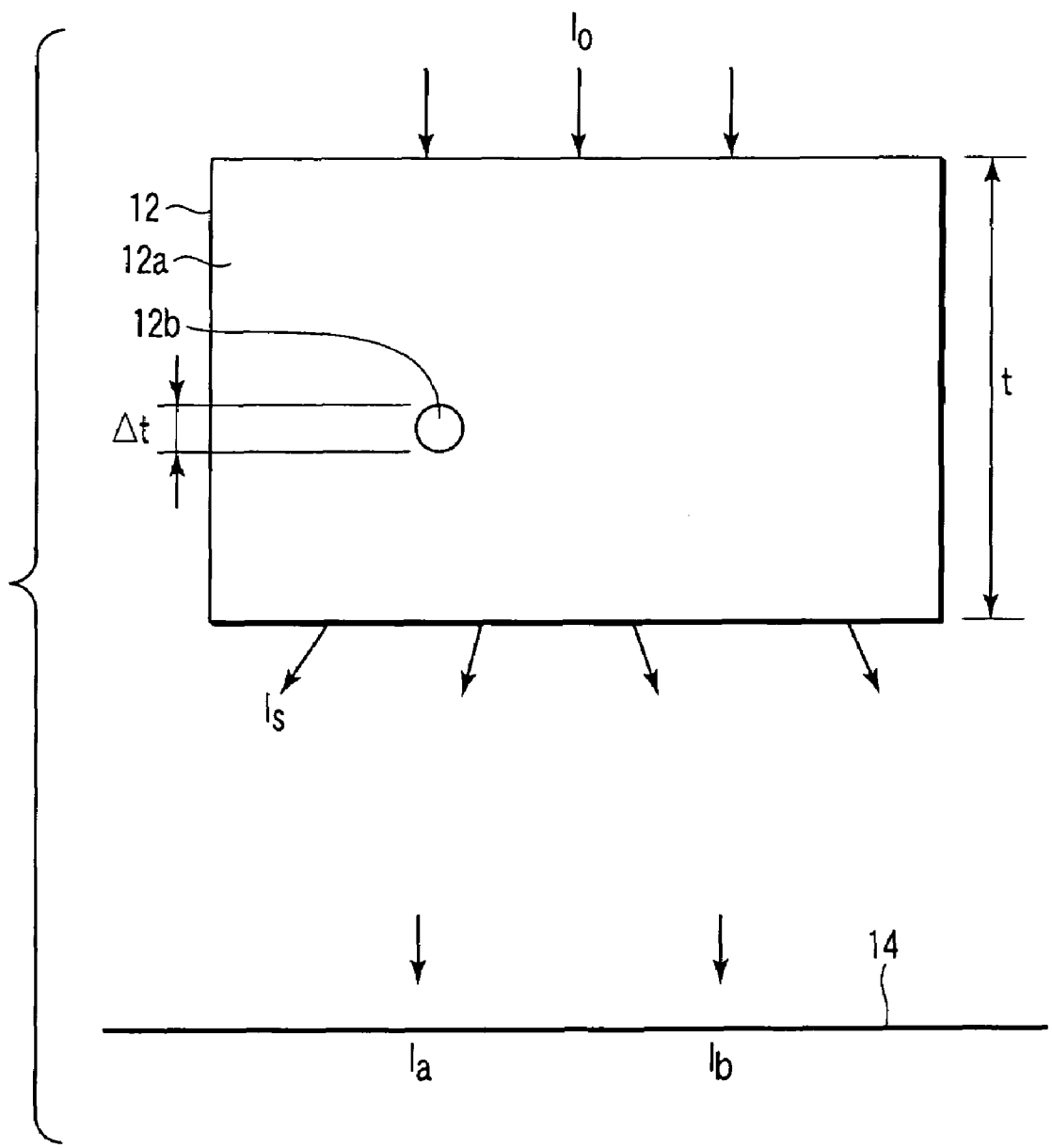
FIG. 8 is a view for explaining the definition of the relationship between the object and the X-rays shown in FIGS. 1 to 3.

As shown in FIG. 8, letting $I_0$ be an incident X-ray dose, $I_a$ be a transmitted X-ray dose through the acrylic resin 12a, $I_b$ be a transmitted X-ray dose though the silica glass ball 12b, Δt be the thickness of the silica glass ball 12b, Δμ be the linear absorptance difference between the acrylic resin 12a and the silica glass ball 12b, and Is be a scattered X-ray dose, an absorption contrast $I_a/I_b$ can be expressed by $$I_a/I_b = 1 − Δt·Δμ·I_0/(I_0+I_S).$$

Note that the influence of the contribution of the scattered rays $I_S$ can be neglected if the enlargement ratio is twice or more.

FIG. 9 shows X-ray absorptance differences, i.e., absorption contrasts, in the relationship between different X-ray energies and the size of the silica glass ball 12b. In this case, for the sake of simplicity, the silica glass ball 12b is regarded as a column having a constant thickness (=diameter d of a sphere) in the transmission direction of X-rays.

The degree to which the small silica glass ball 12b can be identified is determined by not only the size of an absorption contrast but also the amount of X-rays which are transmitted through an object and strike the detector. In other words, this degree is greatly influenced by the number of photons of incident X-rays per unit area on the detector. With the same number of photons and the same absorption contrast, as the size of the silica glass ball 12b decreases, it becomes more difficult to identify.

In the range of X-ray doses allowed in mammography, the limit diameter of a calcified substance to be identified is about 0.02 cm. An X-ray spectrum from a conventional X-ray tube for mammography has a peak value due to characteristic X-rays at about 17 keV, and the tube voltage is set within the range of 20 to 39 kV. Therefore, the average energy of X-rays is about 15 to 20 keV. As shown in FIG. 9 as well, this makes it possible to estimate that even the minimum absorption contrast of a calcified substance having a diameter of 0.02 cm which is identified by mammography is about 8.7%. Note that the above description is associated with the absorption contrast of the acrylic resin 12a with Δt=0.02 cm with respect to an X-ray energy of 20 keV. FIG. 9 is a view showing calculated values based on the assumption of various kinds of simplifications. Approximate estimated values can be obtained from this view.

In the field of mammography applications, Jpn. Pat. Appln. KOKAI Publication No. 2001-194738 discloses that when an X-ray refraction image formed in a region along the contour of the boundary surface between a minute calcified substance and neighboring tissue due to the refraction of an X-ray beam by the boundary surface is superimposed on this X-ray absorption image, the contour of a boundary surface portion is enhanced, and a sharper image can be obtained.

However, the merits obtained by performing imaging upon raising the average energy of X-rays to 15 or 20 keV or more are not described in the above patent reference.

A case wherein imaging is performed upon raising the average energy of X-rays to 15 or 20 keV or more will be described next, together with its effect. In the X-ray examination apparatus 11 of this embodiment, the tube voltage of the X-ray tube 13 is set such that the absorptance difference falls with the range of 5% or less. In practice, the tube voltage of the X-ray tube 13 is increased to increase the X-ray energy as compared with the prior art.

Figure 10:
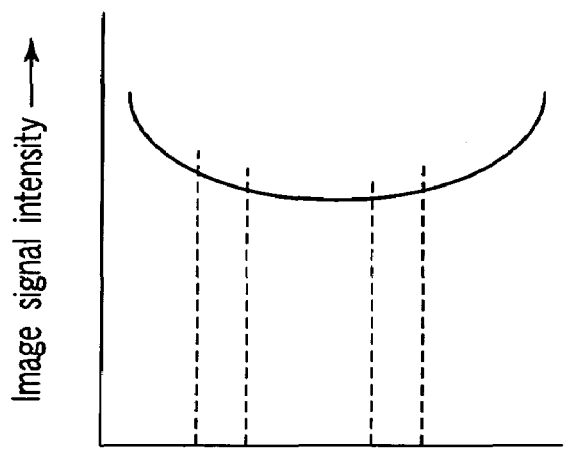
FIG. 10 is a view for explaining a transmitted X-ray image detected by the above detector.
Figure 11:
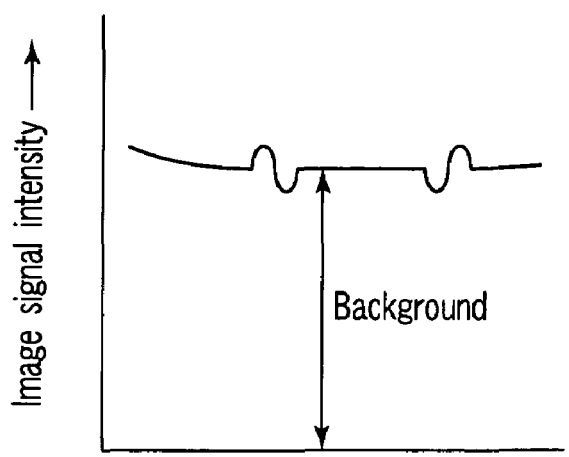
FIG. 11 is a partially enlarged view of an original image formed from the above transmitted X-ray image.

FIG. 10 schematically shows a transmitted X-ray image of the object 12 which is detected by the detector 14 when the X-ray tube 13 whose tube voltage is set such that the X-ray absorptance difference falls within the range of 5% or less applies an X-ray beam to the object 12 in FIG. 1. The original image forming unit 16 forms the original image shown in FIG. 11 from this transmitted X-ray image. However, it is difficult to identify an X-ray refraction image component and a background in the original image.

Figure 12:
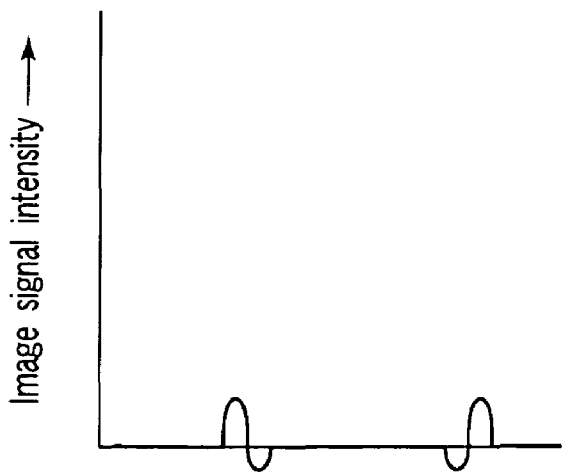
FIG. 12 is a view after image correction processing for the above original image.

As shown in FIG. 12, therefore, the image processing unit 17 performs digital image correction processing of extracting an X-ray refraction image component in the original image. As this digital image correction processing, for example, high-frequency enhancement processing of enhancing the high-frequency component of the original image can be used. In addition, performing subtraction processing of partially subtracting the background image from which the X-ray refraction image before this digital correction processing is excluded from the original image makes it possible to obtain the effect of more accurately extracting an X-ray refraction image component from the original image. As at least part of the background image subtracted from the original image, one of the following can be effectively used: an image obtained by enhancing the low-frequency component of the original image by frequency enhancement processing, an image obtained by sampling pixels more roughly than for the original image, and an image obtained by smoothing a digital image obtained by sampling pixels more roughly than for the original image by using an approximate curved surface (e.g., a two-dimensional polynomial approximated by using the least squares method). In addition, digital image correction processing may be image sharpening processing using a Laplacian transformation or the like.

By extracting only a refraction image component by digital image correction processing and displaying the extracted image on the display unit 18 or the like in this manner, the silica glass ball 12b can be clearly identified. In addition, the number of X-ray photons which contribute to an X-ray refraction image component is larger than that which contributes to an X-ray refraction image component in the prior art, and hence X-ray quantum noise is reduced. Therefore, the silica glass ball 12b can be clearly identified.

FIG. 13 shows X-ray transmittances ($\exp(-\mu \cdot t)$) and incident doses in the relationship between different X-ray energies and the size of the silica glass ball 12b under the assumption that X-rays emitted from the X-ray tube 13 are monoenergetic radiation. An incident dose is a relative value in a case wherein the transmitted dose is equal to a transmitted dose when the X-ray energy is 20 keV.

Figure 14:
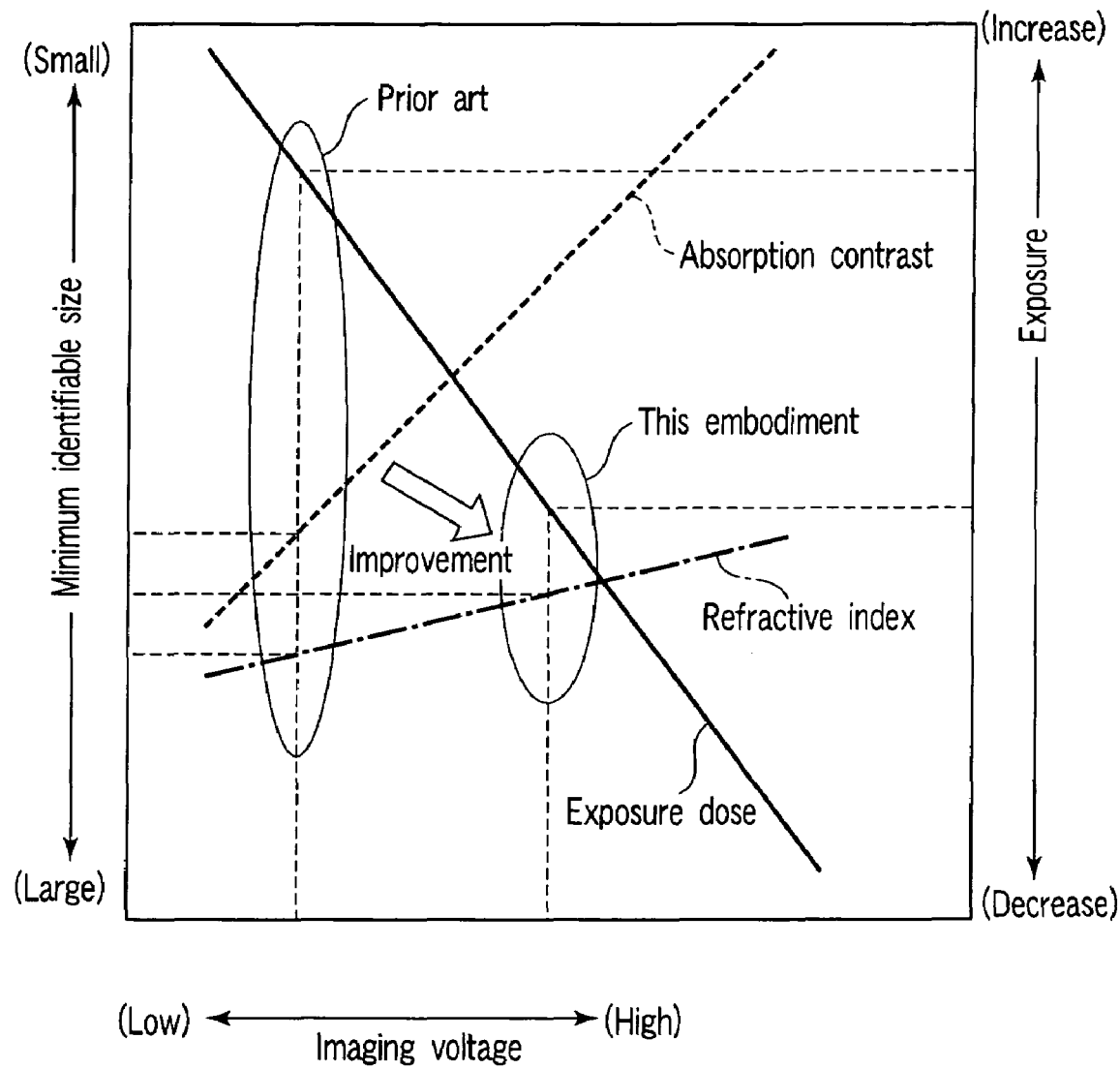
FIG. 14 is a conceptual view showing a merit of the above embodiment with respect to the prior art.

As shown in FIG. 14, since the X-ray transmittance decreases as the X-ray energy decreases, a large incident dose is required for imaging. In addition, since the X-ray transmittance increases as the X-ray energy increases, the incident dose required for imaging can be reduced to a small dose. That is, the exposure dose can be reduced.

In the X-ray examination apparatus 11 according to this embodiment, the tube voltage of the X-ray tube 13 is set such that at least the X-ray absorptance difference between different X-ray propagation media in the object 12 which are to be identified by examination falls within the range of 5% or less, and the tube voltage of the X-ray tube 13 is substantially increased to increase the X-ray energy as compared with the prior art. Therefore, the exposure dose can be reduced as compared with a case wherein a low X-ray energy is set.

Since the tube voltage of the X-ray tube 13 is set to make the X-ray absorptance difference become 5% or less, the identifying power based on the extraction of an X-ray refraction image improves even though the identifying power based on an X-ray absorption image decreases. Therefore, the minute silica glass ball 12b with about Δt=0.02 can be identified. This makes it possible to reduce the exposure and reliably detect even minute abnormalities in the field of medical diagnosis. In addition, in the field of non-destructive examination, even the internal structure of a thick object can be reliably detected.

Although, for example, the exposure can be reduced by setting the tube voltage of the X-ray tube 13 such that the X-ray absorptance difference falls within the range of 10% or less, the tube voltage is preferably set to make the X-ray absorptance difference fall within the range of 8% or less, and more preferably, the range of 4% or less, in order to further reduce the exposure. By setting the tube voltage to make the X-ray absorptance difference to fall within the range of 4% or less, the tube voltage of the X-ray tube 13 is further increased to increase the X-ray energy. Therefore, the exposure dose can be sufficiently decreased.

A case wherein the X-ray examination apparatus 11 is applied to mammography apparatus of imaging the breast as the object 12 will be described next.

Figure 15:
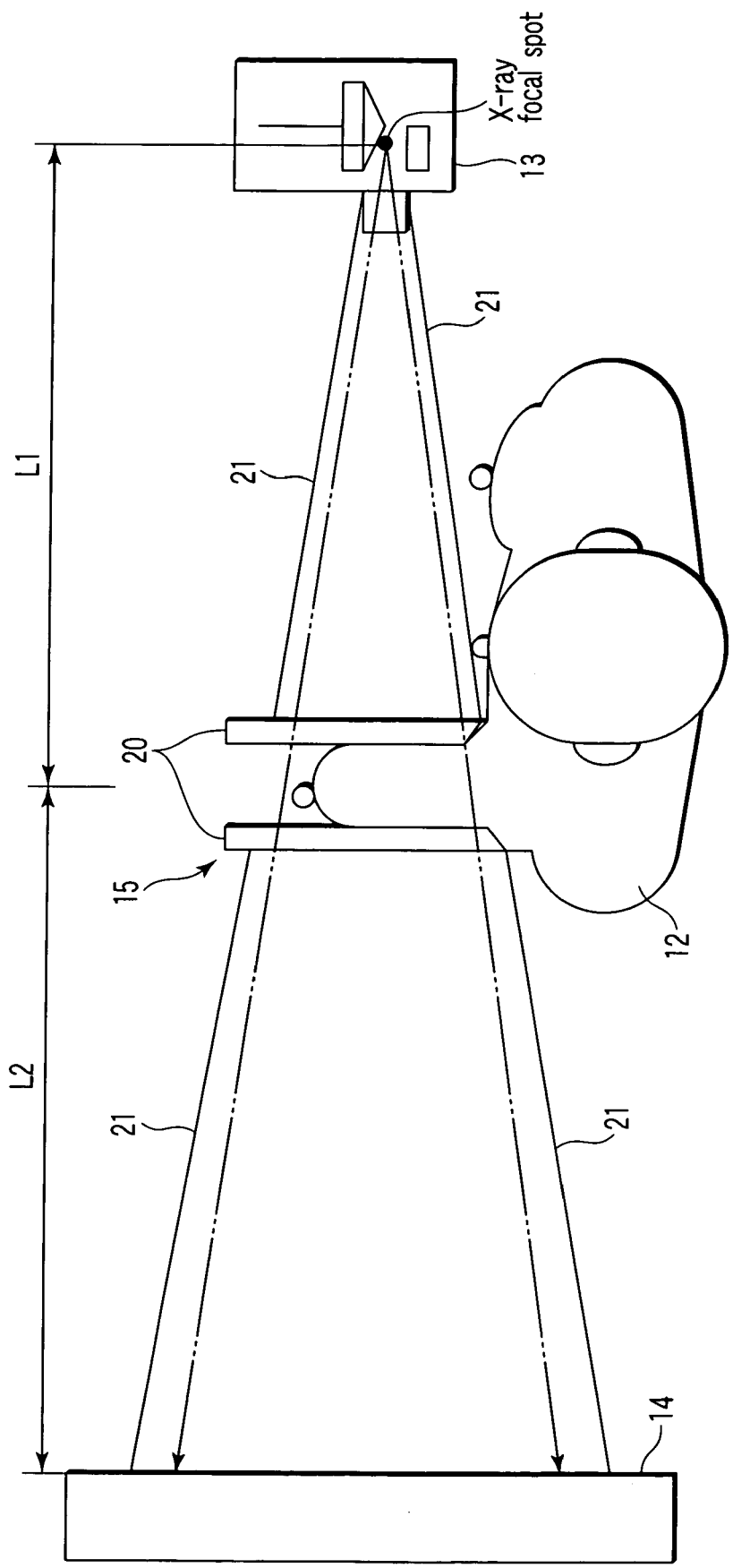
FIG. 15 is a plan view of an embodiment in which the X-ray examination apparatus is applied to mammography apparatus.

As shown in FIG. 15, the X-ray tube 13 is a rotating anode X-ray tube. The focal spot size is 60 μm, and the shape of the focal spot is approximated to a circular focal spot as much as possible instead of a rectangular actual focal spot as in the prior art in order to set a uniform focal spot size in the entire irradiation field. The shaft and the target focal track surface are subjected to coaxial processing and formed to reduce shaft deflection upon rotation. The anode surface is made of a tungsten (W)-rhenium (Re) alloy, the anode inclination angle is 12°, the diameter of the anode focal plane is 120 mm, and the number of revolutions of the anode is 180 rps. The tube voltage of the X-ray tube 13 is set within the range of 40 to 150 kVp.

As the detector 14, a storage phosphor, solid-state imaging device, X-ray image tube, or the like can be used. This makes it possible to have sufficiently high quantum detection efficiency with respect to high-energy components as compared with the prior art. When, for example, an X-ray image tube is to be used, aluminum can be used instead of beryllium for an incident window and input fluorescent film substrate. Beryllium is expensive even for mammography apparatus application. If, a cesium iodide fluorescent substance is used as an input fluorescent film, the fluorescent film thickness is preferably set to be 100 μm or more to increase the quantum detection efficiency of a high energy X-ray component or be 500 μm or less to ensure a resolution of 0.1 mm or less at the fluorescent film surface.

The distance L1 between the X-ray tube 13 and the object 12 is 65 cm, and the distance L2 between the object 12 and the detector 14 is 75 cm. The arrangement adjusting unit 15 has a pinching portions 20 which pinch the breast. A lead cone 21 is provided around an X-ray application range from the X-ray tube 13 to the detector 14.

In conventional mammography, since low-energy X-rays are used by setting the tube voltage of the X-ray tube 13 to 20 to 39 kVp, the exposure dose has been high. In contrast, in this embodiment, since the tube voltage of the X-ray tube 13 is increased to 40 to 150 kVp, and more preferably to 60 to 100 kVp to set the tube voltage of the X-ray tube 13 such that the X-ray absorptance difference falls within the range of 10% or less in mammography, the exposure dose can be reduced by using high-energy X-rays.

Even if imaging is performed at a high tube voltage that allows transmission through even normal tissue of the object 12, since the contour of a minute calcified substance can be extracted, a further minute calcified substance can be detected with less exposure than in the prior art. This makes it possible to apply this technique to group cancer screening for people including the younger generation to which such technique could not have been applied, thereby detecting breast cancers in early stages.

In the field of soft tissue medical diagnosis using mammography and the like, a minute calcified substance can be detected even in the thick object 12.

In mammography, even when the details of a morbid region in the object 12 for which detailed examination is required are to be imaged at a low tube voltage as in the prior art, the same X-ray examination apparatus can be used by changing its settings.

In group X-ray examination directed to a given anticancer measure including mammography, it is desired that the value (merit index) obtained by dividing the number of persons (merit) who are saved from cancer deaths owing to early detection of cancer lesions by X-ray examination by the number of persons (demerit) who died from cancers owing to X-ray examination be 1 or more and be as large as possible. According to the X-ray examination apparatus 11, since the denominator is decreased, and the numerator is increased, the merit index can be reliably increased.

The same effect as that described above can be obtained not only in mammography but also in examination of soft tissue such as the cervical region and limbs.

In addition, in chest examination, even if a region of interest is soft tissue such as a blood vessel or bronchus or an organ through which X-rays are easily transmitted, such as the alveolus, the same effect as that described above can be obtained.

Furthermore, when X-ray examination is to be performed on a blood vessel, renal pelvis system, gallbladder, bile duct, oviduct, lymphatic system, alimentary canal, bronchus, or the like, the exposure dose can be reduced as compared with the prior art, and the amount of high-concentration contrast medium injected in the prior art can be decreased. This allows examination while further reducing the burden on the human body.

The X-ray examination apparatus 11 can also be applied to the field of non-destructive examination, and is effective in examining additives such as glass filler and defects such as voids, in a resin such as plastic or rubber. This apparatus can detect minute additives, foreign substances, and voids inside thicker objects than in the prior art.

Figure 16:
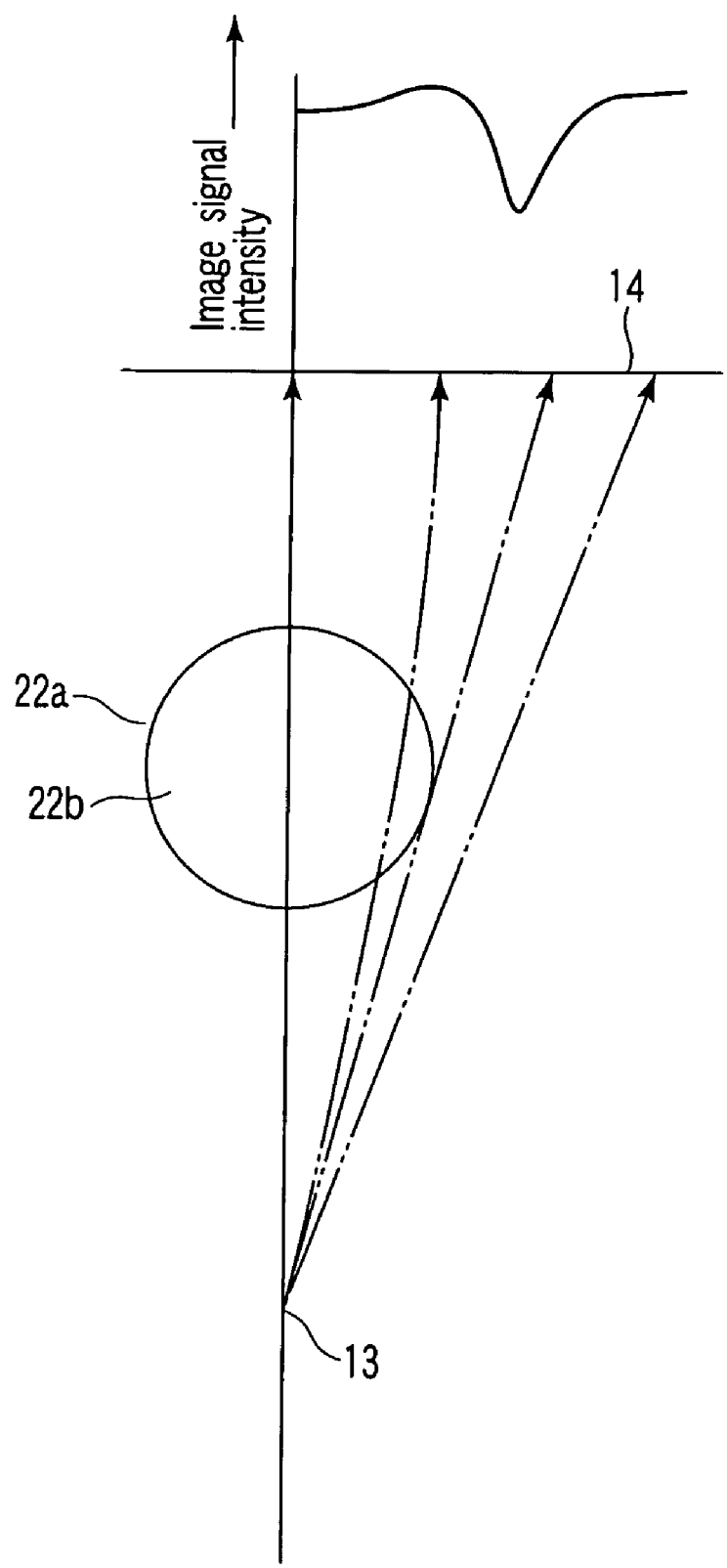
FIG. 16 is a view for explaining a transmitted X-ray image when another X-ray propagation medium in an X-ray propagation medium is a void.

For example, as shown in FIG. 16, in the case of a void 22b in a resin 22a, when an X-ray beam strikes near the boundary surface between the resin and the void, its path deviates to the void side, i.e., to the inside, due to a refraction effect. For this reason, a contour with a high X-ray intensity is formed on the void side of a transmitted X-ray image of the void 22b detected by the detector 14, and a contour with a low X-ray intensity is formed on the resin side. The minimum intensity of this contour or the difference between the maximum intensity and the minimum intensity appears as an X-ray refraction image component.

In the X-ray examination apparatus 11, if the tube voltage of the X-ray tube 13 can be set to a tube voltage that makes the X-ray absorptance difference between different X-ray propagation media in the object 12 exceed 10%, and the object 12 and the detector 14 are adjusted to come into intimate contact with each other by the arrangement adjusting unit 15, examination can be performed under the same examination conditions as those in the prior art.

An X-ray examination method and apparatus according to the second embodiment of the present invention will be described in detail next. Other arrangements of this embodiment are the same as those of the above embodiment. The same reference numerals denote the same parts, and a detailed description thereof will be omitted.

Figure 17:
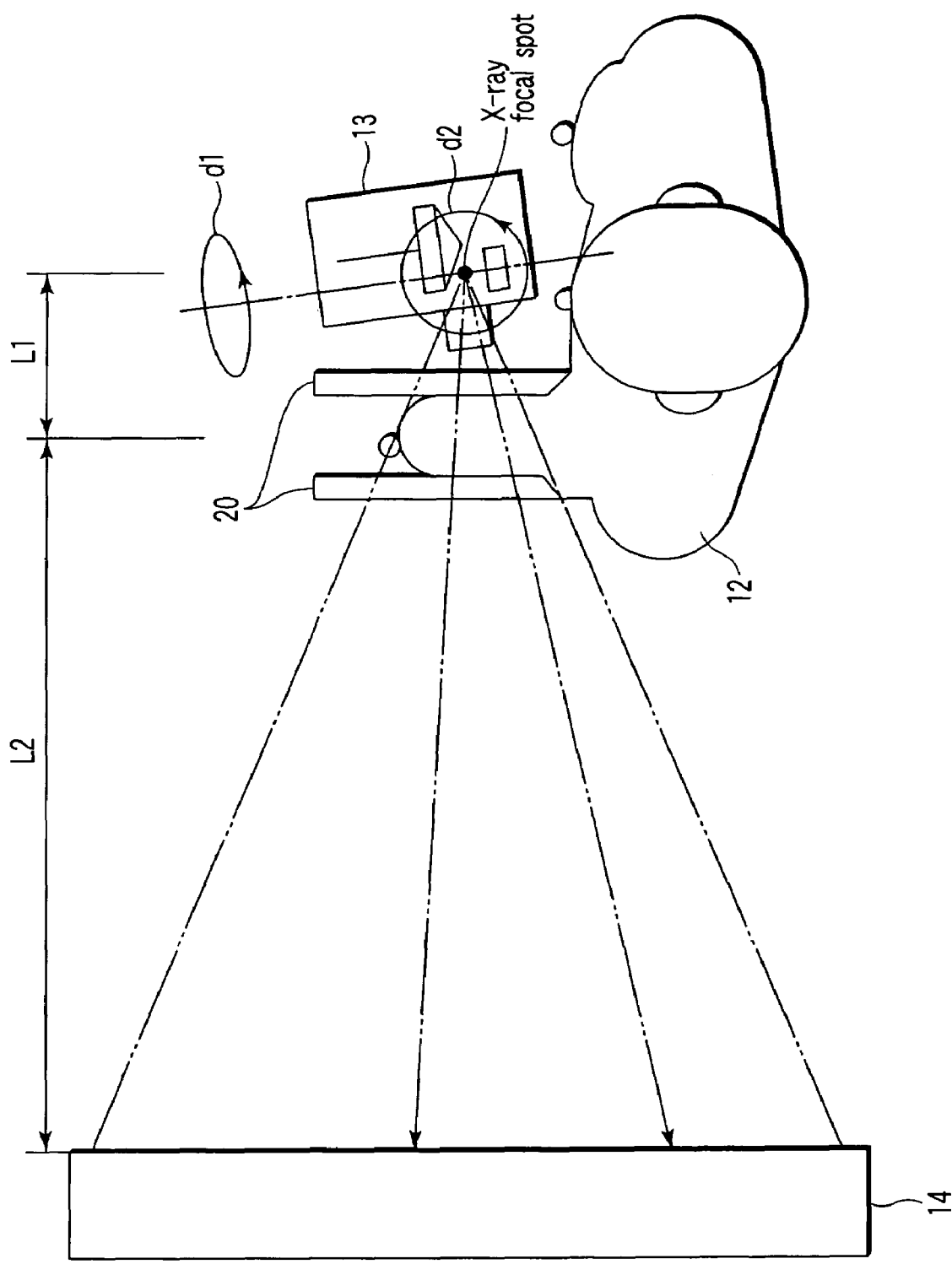
FIG. 17 is a plan view showing an example in which an X-ray examination apparatus according to the second embodiment of the present invention is applied to mammography apparatus.

As shown in FIG. 17, in a mammography apparatus as the X-ray examination apparatus 11, an X-ray tube 13 can be brought close to an object 12 as compared with the X-ray examination apparatus shown in FIG. 15 (note that for the sake of clearer explanation, FIG. 17 exaggeratingly shows a state wherein the X-ray examination apparatus is brought closer to the object than in an actual case). In this embodiment, distance L1=40 cm and distance L2=75 cm.

As the X-ray tube 13, a rotating anode X-ray tube is used, which has a focal spot size of 50 μm. However, unlike in the first embodiment, this focal spot shape is a rectangular shape having a longer length dimension than its widthwise dimension.

Note that in mammography, the tube voltage of the X-ray tube 13 can be set to a tube voltage that makes the X-ray absorptance difference between different X-ray propagation media in the object 12 exceed 10%, examination can be performed while the object 12 and the X-ray tube 13 are brought apart from each other by arrangement adjusting unit 15, as in the prior art.

Assume that the X-ray tube 13 is brought close to the object 12. In this case, if the application range is enlarged, and an X-ray beam is applied to the object 12, effective focal spot sizes viewed from the respective points of a detector 14 greatly vary. In particularly, an effective focal spot size at a peripheral position becomes undesirably large. In the above case, therefore, the X-ray application range of the object 12 is divided into a plurality of regions, and an X-ray beam focused for each region is applied. At the same time, the posture of the X-ray tube is changed so as not to undesirably increase the effective focal spot size. The posture of the X-ray tube is changed by slight rotational movement made almost about the focal position of the X-ray tube. When the object 12 is to be divisionally imaged a plurality of times, the X-ray tube 13 itself is rotated in a first direction d1 and a second direction d2 to apply an X-ray beam to a plurality of portions of the object 12.

Figure 18:
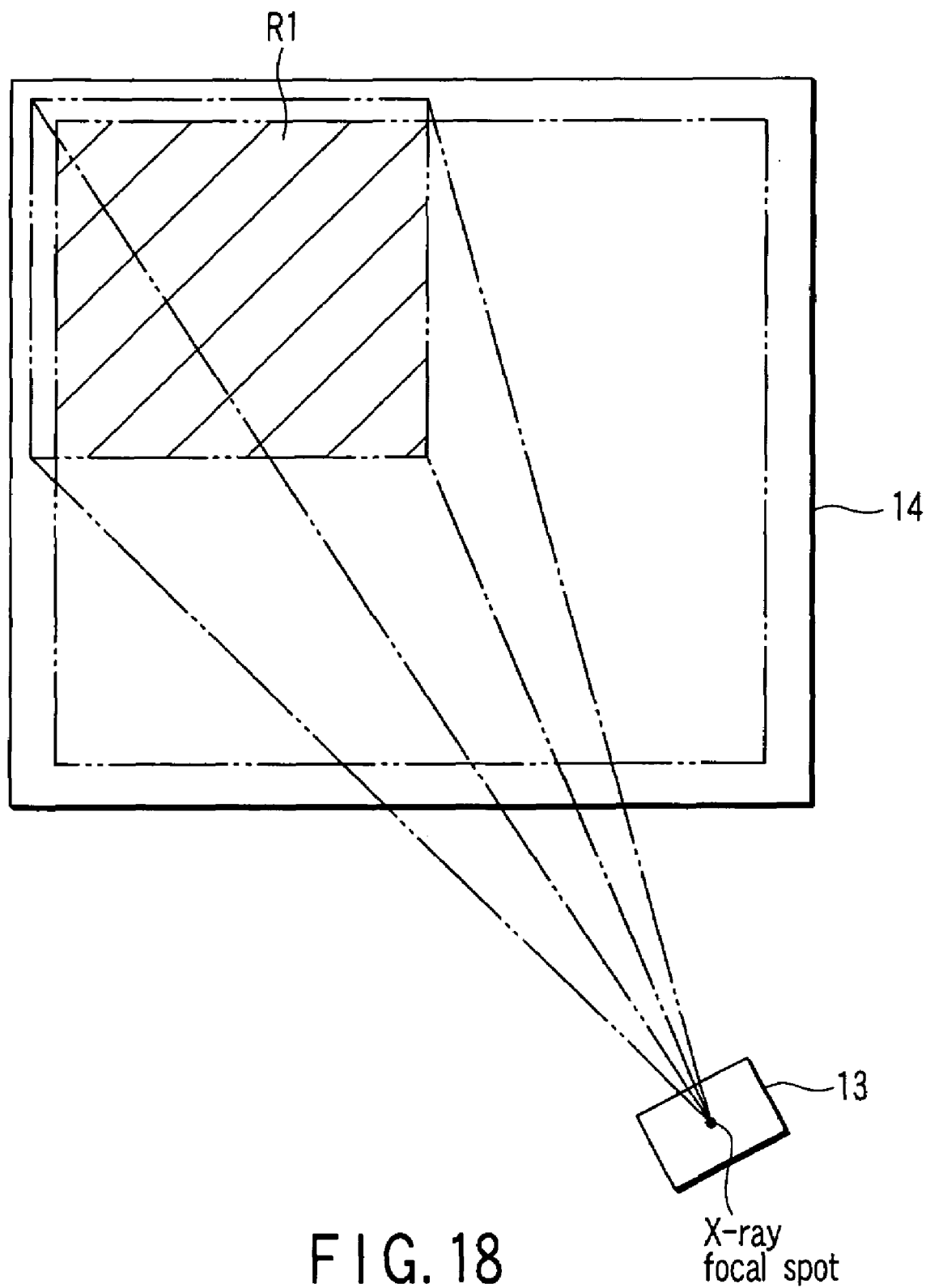
FIG. 18 is a view showing a state wherein the first transmitted X-ray image is detected when the first region of an object is imaged by using the mammography apparatus shown in FIG. 17.
Figure 19:
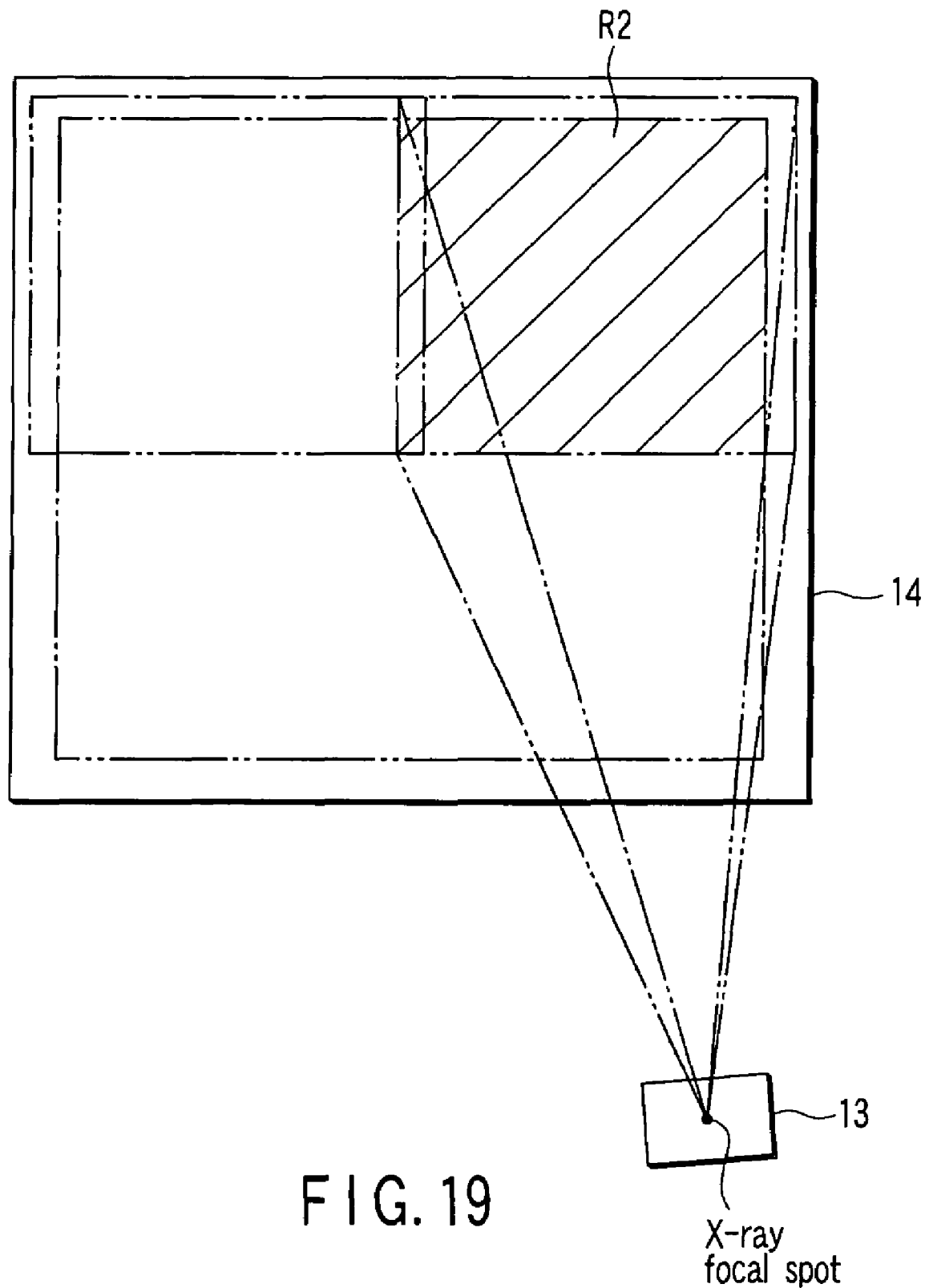
FIG. 19 is a view showing a state wherein the second transmitted X-ray image is detected when the second region of the object is imaged following the operation in FIG. 18.

Assume that the object 12 is to be divisionally imaged four times. In this case, as shown in FIGS. 17 and 18, an X-ray beam is applied to the first region of the object 12 to form the first transmitted X-ray image in a first effective region R1 of the detector 14. As shown in FIG. 19, the X-ray tube 13 is rotated in the second direction d2, and an X-ray beam is applied to the second region of the object 12 to form the second transmitted X-ray image in a second effective region R2 of the detector 14. In this case, the X-ray beam is superimposedly applied to part of the first region of the object 12 to form the second transmitted X-ray image in superimposition on part of the first effective region R1 of the detector 14.

Figure 20:
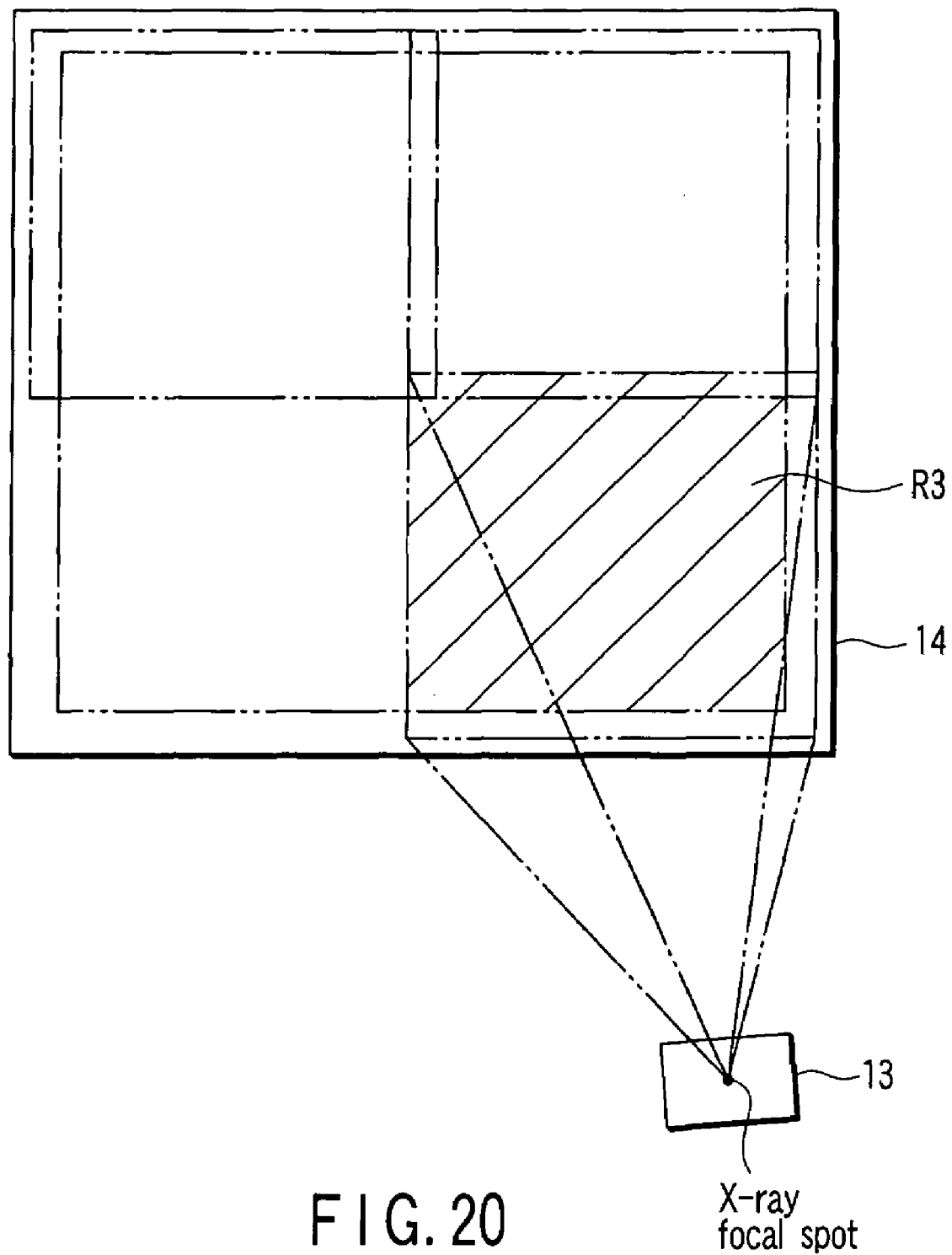
FIG. 20 is a view showing a state wherein the third transmitted X-ray image is detected when the third region of the object is imaged following the operation in FIG. 19.
Figure 21:
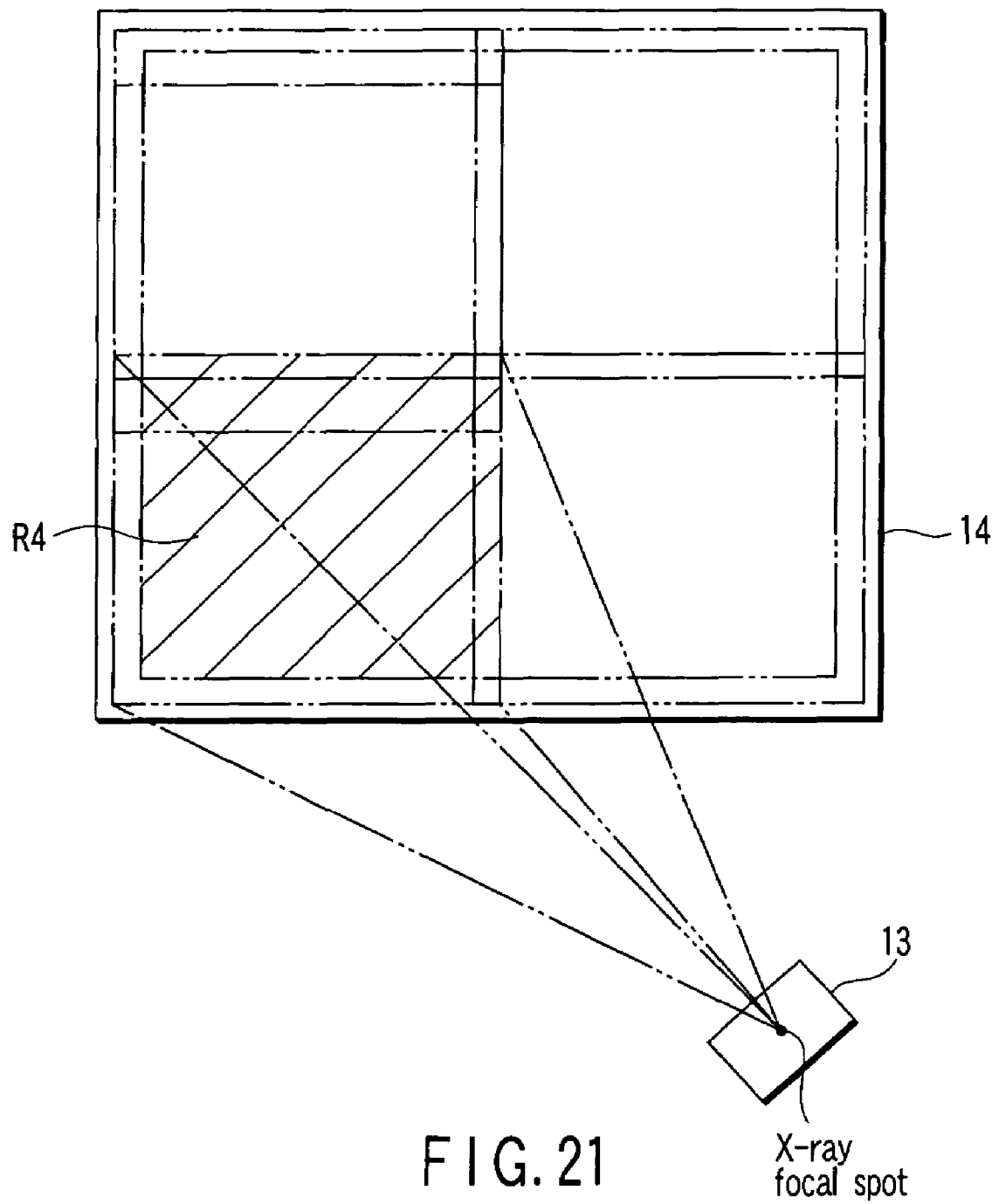
FIG. 21 is a view showing a state wherein the fourth transmitted X-ray image is detected when the fourth region of the object is imaged following the operation in FIG. 20.

As shown in FIG. 20, the X-ray tube 13 is rotated in the first direction d1, and an X-ray beam is applied to the third region of the object 12 to form the third transmitted X-ray image in a third effective region R3 of the detector 14. In this case, the X-ray beam is superimposedly applied to parts of the first and second regions of the object 12 to form the third transmitted X-ray image in superimposition on parts of the first and second effective regions R1 and R2 of the detector 14. As shown in FIG. 21, then, the X-ray tube 13 is rotated in the second direction d2, and an X-ray beam is applied to the fourth region of the object 12 to form the fourth transmitted X-ray image in a fourth effective region R4 of the detector 14. In this case, the X-ray beam is superimposedly applied to parts of the first, second, and third regions of the object 12 to form the fourth transmitted X-ray image in superimposition on parts of the first, second, and third effective regions R1, R2, and R3 of the detector 14.

As described above, the X-ray tube 13 changes the application direction of an X-ray beam and its posture to divisionally image the object 12 a plurality of times while changing the X-ray beam application range. Note that the image processing unit 17 for mammography has an image combining unit which forms a transmitted X-ray image by combining a plurality of images obtained by imaging an object a plurality of times while changing the X-ray beam application range. This makes it possible to obtain a transmitted X-ray image formed by combining a plurality of images which are sensed while the X-ray beam application range is changed.

According to the X-ray examination apparatus having the above arrangement and the X-ray examination method, the object 12 is imaged while the X-ray tube 13 is located closer to the object 12, and the focal spot shape has a rectangular shape with a longer length dimension than its width dimension, thereby reducing the heat load on the X-ray tube. In this case as well, the same effects as those obtained by the X-ray examination apparatus and method according to the first embodiment described above can be obtained. In the field of medical diagnosis, therefore, the exposure can be reduced, and even minute abnormalities can be detected. In the field of non-destructive examination, the internal structure of even a thick object can be reliably detected.

Note that the present invention is not limited to the above embodiments, and can be variously modified within the scope of the present invention. For example, in FIG. 17, imaging may be executed upon setting the distance between the X-ray tube 13 and the object 12 to almost the distance in FIG. 15 without bringing them close to each other. In addition, for example, in FIG. 17, the focal spot size of the X-ray tube 13 is approximated to that of a circular focal spot as much as possible, and the X-ray beam application range is changed by moving the X-ray shielding member. However, the posture of the X-ray tube need not be changed. In addition, for example, as shown in FIG. 22, a mammography apparatus as the X-ray examination apparatus 11 may have an X-Y driving unit 30. The X-Y driving unit 30 can move the detector 14 in the X and Y directions which are perpendicular to each other. For this reason, moving the detector 14 into the application area of an X-ray beam using the X-Y driving unit 30 allows the detector 14 to detect a transmitted X-ray image without omission. Therefore, the mammography apparatus can properly image an object even by using the detector 14 with a small size instead of using the detector 14 with a large size like that shown in FIG. 17. This makes it possible to realize a more inexpensive X-ray examination apparatus.

In addition, although a rotating anode X-ray tube is used as the X-ray tube 13 in all the embodiments described above, a fixed anode X-ray tube or transmission X-ray tube or an X-ray source other than an X-ray tube can be used.

According to the present invention, since the tube voltage of the X-ray tube is set to a tube voltage that makes the X-ray absorptance difference between different X-ray propagation media in an object become 10% or less, the identifying power based on an X-ray absorption image reflecting the X-ray absorbing power difference between the different X-ray propagation media in the object deteriorates. However, identification can be performed by using an X-ray refraction image formed in a region along the contour of the boundary surface between different X-ray propagation media owing to the refraction of an X-ray beam by the boundary surface. In the field of medical diagnosis, therefore, the exposure can be reduced, and even small abnormalities can be reliably detected. In the field of non-destructive examination, the inner structure of even a thick object can be reliably detected.

What is claimed is:

1. An X-ray examination method comprising:

setting a tube voltage of an X-ray tube to a tube voltage that makes an X-ray absorptance difference between a first X-ray propagation medium and a second X-ray propagation medium with an X-ray absorbing power different from that of the first X-ray propagation medium in an object become not more than 10%;

applying an X-ray beam from the X-ray tube to the object while a tube voltage of the X-ray tube is set to the tube voltage; and detecting a transmitted X-ray image including an X-ray refraction image formed in a region along a contour of a boundary surface between the first X-ray propagation medium and the second X-ray propagation medium by refraction of the X-ray beam by the boundary surface in superimposition on an X-ray absorption image reflecting the X-ray absorbing power difference between the first X-ray propagation medium and the second X-ray propagation medium.

2. A method according to claim 1, further comprising:

image processing of extracting the X-ray refraction image component from the transmitted X-ray image.

3. A method according to claim 2, wherein the image processing includes frequency enhancement processing of enhancing a high-frequency component of the transmitted X-ray image.

4. A method according to claim 2, wherein the image processing comprises image sharpening processing.

5. A method according to claim 2, wherein the image processing includes subtraction processing of at least partially subtracting a background image from which the X-ray refraction image is excluded from the transmitted X-ray image.

6. A method according to claim 5, wherein a low-frequency component of the transmitted X-ray image is enhanced in at least part of the background image by frequency enhancement processing.

7. A method according to claim 5, wherein at least part of the background image is obtained by sampling pixels more roughly than for the transmitted X-ray image.

8. A method according to claim 1, wherein when a tube voltage is set for the X-ray tube, the tube voltage of the X-ray tube is set to 40 to 150 kVp if the object is a breast.

9. A method according to claim 1, wherein the transmitted X-ray image is obtained by combining a plurality of images sensed a plurality of times while an application range of the X-ray beam is changed.

10. An X-ray examination apparatus comprising:
an X-ray tube which applies an X-ray beam to an object and a controller configured to set a tube voltage to make an X-ray absorptance difference between a first X-ray propagation medium and a second X-ray propagation medium with an X-ray absorbing power different from that of the first X-ray propagation medium in an object become not more than 10%;
a detector which detects a transmitted X-ray image transmitted through the object; and
an arrangement adjusting unit which sets a distance between the X-ray tube and the object and a distance between the object and the detector so as to obtain the transmitted X-ray image including an X-ray refraction image formed in a region along a contour of a boundary surface between the first X-ray propagation medium and the second X-ray propagation medium by refraction of the X-ray beam by the boundary surface in superimposition on an X-ray absorption image reflecting the X-ray absorbing power difference between the first X-ray propagation medium and the second X-ray propagation medium.

11. An apparatus according to claim 10, further comprising:
an image processing unit which extracts the X-ray refraction image component from the transmitted X-ray image detected by the detector.

12. An apparatus according to claim 10, wherein a tube voltage of the X-ray tube is set to 40 to 150 kVp if the object is a breast.

13. An apparatus according to claim 10, wherein the X-ray tube changes an application direction of the X-ray beam to allow the object to be divisionally imaged a plurality of times while an application range of the X-ray beam is changed.

14. An apparatus according to claim 13, wherein an application direction of the X-ray beam is changed by rotating the X-ray tube about a focal position.

15. An apparatus according to claim 13, wherein the detector is adapted to move to receive all X-ray beams within an application range of the X-ray beam in conjunction with a change in the application direction of the X-ray beam.

16. An apparatus according to claim 13, further comprising:
an image combining unit which forms the transmitted X-ray image by combining a plurality of images obtained by imaging the object a plurality of times while changing the application range of the X-ray beam.

17. An apparatus according to claim 10, wherein letting p(J) be a maximum span dimension of a projection image of an X-ray focal spot which is transmitted through the object in the application direction J, and P is a set of p(J) throughout all application direction of the X-ray transmitted through the object, p(J)<100 μm for all the directions J, and maximum (P)/minimum (P)<2.

18. An apparatus according to claim 10, wherein
the X-ray tube is adapted to set a tube voltage such that an X-ray absorptance difference between the first X-ray propagation medium and the second X-ray propagation medium becomes larger than 10%, and
the arrangement adjusting unit is adapted to make adjustment to bring the object and the detector into intimate contact with each other.

19. An apparatus according to claim 10, wherein
the X-ray tube is adapted to set a tube voltage that makes an X-ray absorptance difference between the first X-ray propagation medium and the second X-ray propagation medium become larger than 10%, and
the arrangement adjusting unit is adapted to make adjustment to bring the object and the X-ray tube close to each other.

* * * * *